United States Patent
Goldammer et al.

(10) Patent No.: US 11,967,417 B2
(45) Date of Patent: Apr. 23, 2024

(54) SYSTEM WITH A SMART FILTRATION AND/OR DIFFUSION DEVICE

(71) Applicant: GAMBRO LUNDIA AB, Lund (SE)

(72) Inventors: Till Goldammer, Bisingen (DE); Thomas Ertl, Bisingen (DE)

(73) Assignee: GAMBRO LUNDIA AB, Lund (SE)

( * ) Notice: Subject to any disclaimer, the term of this patent is extended or adjusted under 35 U.S.C. 154(b) by 613 days.

(21) Appl. No.: 17/263,309

(22) PCT Filed: Jul. 29, 2019

(86) PCT No.: PCT/EP2019/070310
§ 371 (c)(1),
(2) Date: Jan. 26, 2021

(87) PCT Pub. No.: WO2020/025516
PCT Pub. Date: Feb. 6, 2020

(65) Prior Publication Data
US 2021/0158953 A1    May 27, 2021

(30) Foreign Application Priority Data
Jul. 30, 2018  (EP) ..................... 18186215

(51) Int. Cl.
| | | |
|---|---|---|
| *G16H 40/20* | (2018.01) | |
| *G06K 7/10* | (2006.01) | |
| *G06K 19/07* | (2006.01) | |
| *G06Q 10/0639* | (2023.01) | |
| *G16H 40/40* | (2018.01) | |
| *G16H 40/67* | (2018.01) | |
| *A61M 1/14* | (2006.01) | |
| *A61M 1/34* | (2006.01) | |

(52) U.S. Cl.
CPC ......... *G16H 40/20* (2018.01); *G06K 7/10297* (2013.01); *G06K 19/0723* (2013.01); *G06Q 10/06395* (2013.01); *G16H 40/40* (2018.01); *G16H 40/67* (2018.01); *A61M 1/14* (2013.01); *A61M 1/34* (2013.01); *A61M 2205/3553* (2013.01); *A61M 2205/52* (2013.01); *A61M 2205/60* (2013.01)

(58) Field of Classification Search
CPC ........ G16H 40/20; G16H 40/40; G16H 40/67; G16H 40/63; G16H 20/40; G06K 7/10297; G06K 19/0723; G06Q 10/06395; A61M 1/14; A61M 1/34; A61M 2205/3553; A61M 2205/52; A61M 2205/60; H04B 5/0062; H04B 5/0031; H04W 4/80
See application file for complete search history.

(56) References Cited

U.S. PATENT DOCUMENTS

| | | | |
|---|---|---|---|
| 11,147,914 B2 * | 10/2021 | Estes | A61M 5/158 |
| 11,151,223 B1 * | 10/2021 | Lee | G16H 20/17 |
| 11,224,841 B2 * | 1/2022 | Fulkerson | A61M 1/1692 |
| 2013/0087609 A1 * | 4/2013 | Nichol | G06F 16/23 |
| | | | 235/375 |
| 2014/0115101 A1 | 4/2014 | Wittner et al. | |
| 2015/0269327 A1 | 9/2015 | Lyons et al. | |
| 2015/0287041 A1 | 10/2015 | Davis et al. | |
| 2017/0021306 A1 * | 1/2017 | Fulkerson | A61M 1/3639 |
| 2017/0237467 A1 * | 8/2017 | Rovatti | G06K 19/06112 |
| | | | 455/41.3 |
| 2017/0239412 A1 * | 8/2017 | Court | H04B 5/0031 |
| 2019/0271681 A1 * | 9/2019 | McKirdy | G06K 19/0723 |
| 2021/0110920 A1 * | 4/2021 | Heyes | A61M 1/34 |

OTHER PUBLICATIONS

PCT Search Report and Written Opinion prepared for PCT/EP2019/070310, completed Oct. 8, 2019.

* cited by examiner

*Primary Examiner* — An T Nguyen
(74) *Attorney, Agent, or Firm* — Barnes & Thornburg LLP

(57) ABSTRACT

The present disclosure relates to a system comprising a filtration and/or diffusion device and an editable dataset comprising data pertaining to the filtration and/or diffusion device.

9 Claims, No Drawings

SYSTEM WITH A SMART FILTRATION AND/OR DIFFUSION DEVICE

CROSS-REFERENCE TO RELATED APPLICATIONS

This application is the U.S. national phase of PCT/EP2019/070310, filed on Jul. 29, 2019, which claims the benefit of European Patent Application Serial Number 18186215.2, filed on Jul. 30, 2018, the entire disclosures of both of which are incorporated herein by reference.

TECHNICAL FIELD

The present disclosure relates to a system comprising a filtration and/or diffusion device and an editable dataset comprising data pertaining to the filtration and/or diffusion device.

BACKGROUND OF THE INVENTION

Hemodialyzers commercially available today do not offer automated identification, storage and tracking of product data and production data. Important product information, such as the instructions for use, the expiration date, batch labels or quality information only are provided as hard copies.

Also, it is not possible to digitally disable a hemodialyzer in case of quality problems to prevent its use. Thus, currently the hemodialyzer does not offer additional benefits to the patient or the clinical staff that go beyond the therapy itself.

US 2017/0239412 A1 discloses a method of establishing a wireless operating communication between an extracorporeal blood treatment device and a medical accessory. The method comprises the steps of establishing a wireless auxiliary communication between the blood treatment device and the medical accessory, transferring configuration data using the wireless auxiliary communication and establishing the wireless operating communication between the blood treatment device and the medical accessory based on the configuration data.

US 2015/235065 A1 relates to the use of RFID to enable authentication and validation of an electrode array by a sensing patient interface cable. An electrode, electrode array or physiological measuring device, bearing a passive RFID transponder, or tag, is detected and provides stored data to a RFID interrogator and then to an associated physiological monitoring system. The data include the manufacturer, information about the manufacturing history and the use history of the electrode array for the purposes of authenticating the electrode array source and verifying that the electrode array meets the criteria for use (e.g. before expiration date, number of previous uses, etc.). Data that relate to calibration may also be programmed.

US 2004/008123 A1 discloses a system for monitoring medical devices, such as pharmaceuticals and prescriptions, that utilizes Radio-Frequency Identification (RFID) techniques. The system includes an RFID tag associated with the medical device, the tag programmed with information about the device, such as data about the manufacture, distribution, and sale thereof. The system further includes a reader that interrogates the tag and updates a database regarding the condition of the tag. The information in the tag can be revised by the reader or by an associated detector as the condition of the medical device changes, such as its location, sale, use, shelf life, and disposal.

US 2014/115101 A1 provides a method, control module and extracorporeal blood treatment apparatus for transferring data from said extracorporeal blood treatment apparatus. Data is retrieved pertaining to an operation of the apparatus, the data is encoded into a machine readable graphical representation for decoding at a remote server to recover the retrieved data and displaying the machine readable graphical representation as an image on the display to allow capture of the displayed image with an image capturing device and transmission of the image from the image capturing device to a remote server over a communication channel.

US 2013/087609 A1 discloses methods and systems for accurately tracking medical devices using a two-dimensional (2D) matrix code. Scan data, location data, and status data may be received by a processor. The scan data may comprise identification information corresponding to a medical device; the location data may comprise location information corresponding to the medical device; and the status data may comprise status information corresponding to the medical device. Once the scan data, location data, and status data has been received, the scan data, the location data and the status data may be stored. Next, at least one medical-device characteristic may be determined, based on at least the scan data and the status data, and once the medical-device characteristic is determined, the medical-device characteristic may be displayed on a graphical display.

US 2015/269327 A1 teaches a method, computer program product, and computing system for associating a scannable tag with a medical device. Identifying indicia that is obtained by scanning the scannable tag with a client electronic device is received, thus defining an identified medical device. Technical information concerning the identified medical device is provided to the client electronic device.

It would be desirable to have a system which allows for automated identification of a filtration and/or diffusion device as well as for storing, tracking and handling product data and production data pertaining to the filtration and/or diffusion device.

SUMMARY

The present disclosure provides a system comprising a filtration and/or diffusion device and an editable dataset comprising data pertaining to the filtration and/or diffusion device. The dataset is either present in the memory of an RFID chip which is part of the filtration and/or diffusion device; or the dataset is present in a data cloud and is linked to the filtration and/or diffusion device via an identifier which is part of the filtration and/or diffusion device. Read and write operations on the dataset are performed using a device which can read the identifier of the filtration and/or diffusion device and exchange information with the dataset, e.g., a smartphone or a tablet.

DETAILED DESCRIPTION

The present disclosure provides a system comprising a filtration and/or diffusion device and an editable dataset comprising data pertaining to the filtration and/or diffusion device.

In the context of the present disclosure, the term "filtration and/or diffusion device" refers to hemodialyzers, hemofilters and ultrafilters.

In the context of the present disclosure, the term "editable dataset" refers to a set of data fields, each data field comprising data pertaining to the filtration and/or diffusion device, wherein the contents of each data field present in the data set can be altered, i.e., overwritten with other data.

The editable dataset may comprise a plurality of data pertaining to the filtration and/or diffusion device.

In one embodiment, the data pertaining to the dialyzer comprise manufacturing data of the filtration and/or diffusion device. Examples of manufacturing data include lot number, manufacturing date, manufacturing location, parameters of the manufacturing process, properties of the device and its components, e.g. the membrane present in the device, data on raw materials used, data pertaining to sterilization of the device, etc.

In a further embodiment, the data pertaining to the filtration and/or diffusion device comprise an expiration date of the filtration and/or diffusion device.

In another embodiment, the data pertaining to the filtration and/or diffusion device comprise performance data of the filtration and/or diffusion device. Examples of performance data include ultrafiltration rates; liquid flow rate ranges; sieving coefficients of relevant substances, e.g., vitamin B12, inulin, β2-microglobulin, albumin etc.; and clearance data of relevant substances, e.g., urea, creatinine, phosphate, vitamin B12, inulin etc.

In another embodiment, the data pertaining to the filtration and/or diffusion device comprise quality release data of the filtration and/or diffusion device.

In still another embodiment, the data pertaining to the filtration and/or diffusion device comprise instructions for use of the filtration and/or diffusion device like start-up instructions, warnings and cautions, etc.

In another embodiment, the data pertaining to the filtration and/or diffusion device comprise supply chain data of the filtration and/or diffusion device. Examples of supply chain data include tracking data, data on present and past storage locations of the device, storage conditions, environmental parameters, stock numbers, data on sales contacts, etc.

The editable dataset is assigned to the dialyzer via an identifier forming part of the filtration and/or diffusion device. The identifier links the device and the dataset unambiguously, i.e. in a one-to-one relationship.

The identifier forms part of the device. In one embodiment, the identifier is present on an outer surface of the device. For example, the identifier may be present on a label or tag affixed to the device, e.g., glued to the outer surface of the device. In another embodiment, the identifier is embedded in an outer wall of the device, i.e. in the wall of the housing or of an end cap. In still another embodiment, the identifier is located within the device.

In one embodiment, the identifier takes the form of a barcode, a data matrix, a QR code, a color marking, a hologram, or the like. In this embodiment, the identifier is readable by optical readers, e.g., using a scanner or a camera. In another embodiment, the identifier is present in an RFID tag or an NFC tag. In a specific embodiment, the identifier is part of the editable dataset and present in the memory of an RFID or NFC chip forming part of the filtration and/or diffusion device. In this embodiment, the identifier is readable by a radio-frequency receiver.

In one embodiment of the system, a RFID tag or NFC tag attached to the device to be identified is readable by a two-way radio transmitter-receiver (interrogator or reader) which sends a signal to the tag and reads its response.

As NFC tags can have very simple designs and are much cheaper than RFID tags, one embodiment of the system of the present disclosure uses NFC chips rather than RFID chips. However, NFC typically requires a separation of 10 cm or less between reader and tag, while RFID can bridge larger distances.

A RFID or NFC reader transmits an encoded radio signal to interrogate the tag. The tag receives the message and then responds with its identification. Since tags have individual identifiers, the RFID or NFC system can discriminate among several tags that might be within the range of the reader and read them simultaneously.

The RFID tag comprises at least three parts: an integrated circuit that stores and processes information and that modulates and demodulates radio-frequency (RF) signals; a means of collecting DC power from the incident reader signal; and an antenna for receiving and transmitting the signal. The tag information is stored in a non-volatile memory. The RFID tag includes either fixed or programmable logic for processing the transmission and sensor data, respectively.

The RFID tag can be either passive, active or battery-assisted passive. An active tag has an on-board battery and periodically transmits its ID signal. A battery-assisted passive (BAP) has a small battery on board and is activated when in the presence of an RFID reader. A passive tag is cheaper and smaller because it has no battery; instead, the tag uses the radio energy transmitted by the reader.

In one embodiment, an active RFID tag is used. An active RFID tag has an on-board battery and periodically transmits its ID signal. The tag may either be read-only, comprising the identifier that is used as a key to the editable dataset, or may be read/write, where data can be written into the tag by the system user. Field programmable tags may be write-once, read-multiple.

The editable dataset is either present in the memory of a radio-frequency identification device (RFID) or near-field communication (NFC) chip forming part of the filtration and/or diffusion device; or the editable dataset is present in a data cloud.

In one embodiment, the editable dataset is present in the memory of a radio-frequency identification device (RFID) or near-field communication (NFC) chip forming part of the filtration and/or diffusion device. In a specific embodiment, the identifier of the device is also present in the memory of the RFID chip or NFC chip. In a further embodiment, the identifier is part of the editable dataset.

In another embodiment, the editable dataset is present in a data cloud. In one embodiment, the data cloud is accessible by a portable communication device and the editable dataset is readable and editable using the portable communication device. In a further embodiment, the data cloud also is accessible by at least one remote computer or computer network and the editable dataset is readable and editable by the at least one remote computer or computer network. Examples of computers or computer networks that can access the editable dataset in the data cloud include a computer or computer network of a hospital using the filtration and/or diffusion device; a computer or computer network of the manufacturer of the filtration and/or diffusion device; and a computer or computer network performing supply chain management of the filtration and/or diffusion device.

In one embodiment of the system, the editable dataset is accessible and editable by a portable communication device. The portable communication device can read the identifier and access the editable dataset. The portable communication device also is capable of reading data from the editable dataset and writing data to the editable dataset. In a further embodiment, the portable communication device also can establish a connection to at least one remote computer.

In one embodiment, a wireless connection is established, e.g., using a WLAN (Wi-Fi), or a cellular network (GSM, UMTS, LTE). In one embodiment, the connection to the remote computer(s) is established via the internet.

In a further embodiment, the portable communication device is configured to establish a connection to more than one, e.g., two or three, remote computers or computer networks. In one embodiment, connections to more than one computer or computer network are established successively. In another embodiment, connections to more than one computer or computer network are established simultaneously. Examples of computers or computer networks the portable communication device is configured to connect to include a computer or computer network of a hospital using the filtration and/or diffusion device; a computer or computer network of the manufacturer of the filtration and/or diffusion device; and a computer or computer network performing supply chain management of the filtration and/or diffusion device.

In one embodiment, the portable communication device is a smartphone or a tablet computer. In another embodiment, the portable communication device is a scanner device with a wireless connection to at least one remote computer. In still another embodiment, the portable communication device is a reader/writer device comprising a two-way radio transmitter-receiver, a display and a keyboard, optionally also with a wireless connection to at least one remote computer.

The present disclosure also provides a process which facilitates handling and use of data pertaining to a filtration and/or diffusion device. The process comprises the steps of
a) reading an identifier forming part of a filtration and/or diffusion device with a portable communication device;
b) accessing an editable dataset assigned to the filtration and/or diffusion device via the identifier with the portable communication device, the editable dataset being either present in the memory of a radio-frequency identification device (RFID) or near-field communication (NFC) chip forming part of the filtration and/or diffusion device, or being present in a data cloud accessible by the portable communication device;
c) reading data from the editable dataset and/or writing data to the editable dataset with the portable communication device.

In one embodiment, the process further comprises
d) accessing at least one remote computer or computer network with the portable communication device and sending data previously read from the editable dataset to at least one remote computer or computer network and/or writing data previously received from at least one remote computer or computer network to the editable dataset.

In one embodiment of the process, the portable communication device displays data from the editable dataset.

The process of the present disclosure comprises a) reading an identifier forming part of a filtration and/or diffusion device with a portable communication device.

Suitable identifiers forming part of a filtration and/or diffusion device have been described above. Suitable portable communication devices also have been described above.

After the identifier of the filtration and/or diffusion device has been read, it is used to access an editable dataset assigned to the filtration and/or diffusion device using the portable communication device. The editable dataset unambiguously linked to the filtration and/or diffusion device by the identifier comprises data pertaining to the filtration and/or diffusion device.

As already explained, the editable dataset may comprise a plurality of data pertaining to the filtration and/or diffusion device, like manufacturing data of the filtration and/or diffusion device; an expiration date of the filtration and/or diffusion device; performance data of the filtration and/or diffusion device; quality release data of the filtration and/or diffusion device; instructions for use of the filtration and/or diffusion device; and supply chain data of the filtration and/or diffusion device.

In one embodiment of the process, the editable dataset is present in the memory of a radio-frequency identification device (RFID) or near-field communication (NFC) device chip forming part of the filtration and/or diffusion device. The portable communication device is used to read data from the editable dataset present in the memory of the RFID chip or NFC chip and/or write data to the editable dataset. In one embodiment of the process, data read from the memory of the RFID chip or NFC chip is displayed on the portable communication device so that the user of the portable communication device can see and read it. In a further embodiment, the portable communication device accesses at least one remote computer or computer network and sends data previously read from the editable dataset to the at least one remote computer or computer network.

In an embodiment of the process, data entered into the portable communication device by the user is written to the memory of the RFID chip or NFC chip, i.e., the editable dataset is edited and one or more data fields of the editable dataset are overwritten. In a further embodiment, the portable communication device accesses at least one remote computer or computer network to receive data pertaining to the filtration and/or diffusion device and writes data previously received from the at least one remote computer or computer network to the memory of the RFID chip or NFC chip to edit the editable dataset by overwriting one or more of its data fields.

As an example, the portable communication device may establish a connection to a computer or computer network of the manufacturer of the filtration and/or diffusion device and check whether the information pertaining to the filtration and/or diffusion device read from the RFID chip still is up to date. In case an update is required, the current data are written to the RFID chip or NFC chip to update the dataset. In a specific case where a problem has been discovered in a particular lot of filtration and/or diffusion devices, the information received from the computer or computer network of the manufacturer can be used to block use of each and any filtration and/or diffusion device which is part of the lot. As another example, contact information present in the editable dataset can be updated with up-to-date information received from the computer or computer network of the manufacturer.

As another example, the portable communication device may establish a connection to a computer or computer network of a hospital using the filtration and/or diffusion device and send data of the editable dataset, i.e. product data of the filtration and/or diffusion device, to the computer or computer network of the hospital, so that the data can directly be incorporated into the patient file of the person treated with the filtration and/or diffusion device. Also, performance parameters of the filtration and/or diffusion device sent to the computer or computer network of the hospital may be used to set treatment parameters to meet the prescription for the patient.

In another embodiment of the process, the editable dataset is present in a data cloud accessible by the portable communication device. In this embodiment, the portable communication device establishes a connection to the data cloud and accesses the editable dataset to read data from the editable dataset or write data to the editable dataset. Also in this embodiment, the portable communication device may additionally access at least one remote computer or computer network to send or receive data pertaining to the filtration and/or diffusion device. In one embodiment, the portable communication device writes data previously received from the at least one remote computer or computer network to the editable dataset, overwriting one or more of its data fields.

If the editable dataset is present in a data cloud rather than in the memory of an RFID chip or NFC chip forming part of the filtration and/or diffusion device, additional options for editing the dataset become available. For instance, a computer or computer network of the manufacturer of the filtration and/or diffusion device may access the data cloud and modify data in the editable dataset of all filtration and/or diffusion devices of a certain type or in a certain lot, so that each dataset comprises the most recent information, when the corresponding filtration and/or diffusion device next accesses the editable dataset. Also, information from a plurality of datasets pertaining to, for example, all filtration and/or diffusion devices of a certain type or in a certain lot, can be recovered at any time desired.

In one embodiment of the process of the present disclosure, the portable communication device establishes a connection to at least one remote computer or computer network.

In one embodiment of the process, a computer or computer network of a hospital using the filtration and/or diffusion device is accessed.

In another embodiment of the process, a computer or computer network of the manufacturer of the filtration and/or diffusion device is accessed.

In still another embodiment of the process, a computer or computer network used in performing supply chain management of the filtration and/or diffusion device is accessed.

The portable communication device sends data previously read from the editable dataset to the remote computer(s) or computer network(s) and/or writes data previously received from the remote computer(s) or computer network(s) to the editable dataset.

Data sent to a computer or computer network of a hospital using the filtration and/or diffusion device can be used to document use of the filtration and/or diffusion device, e.g., in a patient file; or it can be used for statistical evaluations of a plurality of similar filtration and/or diffusion devices, for instance, for evaluating performance of a certain type of filtration and/or diffusion device, or for evaluating data pertaining to a patient group treated with a certain type of filtration and/or diffusion device; or it can be used for inventory management in the hospital, for example, keeping track of the number of filtration and/or diffusion devices used, so that when the number of devices available drops below a predefined threshold, an order for replenishment of stock is automatically generated and sent to the supplier.

Data sent to a computer or computer network of the manufacturer of the filtration and/or diffusion device can be used for statistical evaluations of a plurality of similar filtration and/or diffusion devices, for instance, for evaluating performance of a certain type of filtration and/or diffusion device; for evaluating data pertaining to a certain lot of filtration and/or diffusion device; for gathering data relevant to a quality system of the manufacturer; or for detecting trends or deviations in the properties of the filtration and/or diffusion devices.

Data sent to a computer or computer network performing supply chain management of the filtration and/or diffusion device can be used for tracking the filtration and/or diffusion device over its entire life cycle; for managing inventory of filtration and/or diffusion devices; or for managing logistics of filtration and/or diffusion devices.

In one embodiment of the process, the editable dataset is present in the memory of a RFID chip or NFC chip forming part of the hemodialyzer, hemofilter or ultrafilter. At least one remote computer or computer network of the manufacturer of the hemodialyzer, hemofilter or ultrafilter is accessed with the portable communication device and data previously read from the editable dataset is sent to at least one remote computer or computer network of the manufacturer of the hemodialyzer, hemofilter or ultrafilter. Data received from at least one remote computer or computer network of the manufacturer of the hemodialyzer, hemofilter or ultrafilter is written to the editable dataset assigned to the hemodialyzer, hemofilter or ultrafilter and is used to block use of the hemodialyzer, hemofilter or ultrafilter in case the manufacturer of the hemodialyzer, hemofilter or ultrafilter has detected a problem with the hemodialyzer, hemofilter or ultrafilter, or storage conditions of the hemodialyzer, hemofilter or ultrafilter or environmental parameters have been outside the allowable limitations.

Writing data previously received from the remote computer(s) or computer network(s) to the editable dataset assigned to the filtration and/or diffusion device may be used to block use of the filtration and/or diffusion device, e.g., in case the manufacturer of the filtration and/or diffusion device has detected a problem with the device, or storage conditions of the device or environmental parameters have been outside the allowable limitations.

Writing data previously received from the remote computer(s) or computer network(s) to the editable dataset assigned to the filtration and/or diffusion device may also be used to update information in the editable dataset or to supplement data present in the editable dataset. For instance, data on the environmental conditions of the filtration and/or diffusion device during its itinerary from the plant to the patient may be added; a destination of the filtration and/or diffusion device may be entered into the dataset; or operating parameters of the filtration and/or diffusion device during treatment may be documented in the editable dataset.

These functionalities and benefits are essentially based on the direct digital exploitation of product-related data such as product labeling, expiry date, quality information, usage instructions at the point of use.

It is an advantage of the system and process of the present disclosure that data pertaining to the filtration and/or diffusion device can be retrieved and edited using standardized devices, such as smartphones or tablet computers. Another advantage is that the data can be updated even after the device has already been labeled and during the entire lifetime of the filtration and/or diffusion device.

The present disclosure provides an allocation of product and production data to the filtration and/or diffusion device over its entire life cycle and automated identification of the filtration and/or diffusion device. The availability of this product and production data benefits all stakeholders involved in the value chain (manufacturer, supplier, logistics, hospitals) and opens opportunities to optimize therapy and develop new business models based on digitally available information. For instance, the active communication of a disposable medical product, such as a dialyzer, can supplement the data flow generated during clinical use of the disposable with product-related data. Furthermore, it allows the manufacturer to locate the product and to record the consumption. This facilitates planning processes for customers, logistics, and manufacturers.

The invention claimed is:

1. A process comprising the steps of
   a) reading an identifier forming part of a hemodialyzer, a hemofilter, or an ultrafilter with a portable communication device;
   b) accessing an editable dataset assigned to the hemodialyzer, the hemofilter, or the ultrafilter via the identifier with the portable communication device, wherein the editable dataset is either present a) in the memory of a RFID chip or a NFC chip forming part of the hemodialyzer, the hemofilter, or the ultrafilter, or b) in a data cloud accessible by the portable communication device;
   c) reading data from the editable dataset and/or writing data to the editable dataset with the portable communication device;
   d) accessing at least one remote computer or computer network with the portable communication device, and either sending data previously read from the editable dataset to at least one remote computer or computer network or writing data previously received from at least one remote computer or computer network to the editable dataset,
   wherein the editable dataset is present in memory of a RFID chip or an NFC chip forming part of the hemodialyzer, the hemofilter, or the ultrafilter,
   wherein at least one remote computer or computer network of the manufacturer of the hemodialyzer, the hemofilter, or the ultrafilter is accessed with the portable communication device, and
   data previously read from the editable dataset is sent to at least one remote computer or computer network of the manufacturer of the hemodialyzer, the hemofilter, or the ultrafilter, and
   data received from at least one remote computer or computer network of the manufacturer of the hemodialyzer, the hemofilter, or the ultrafilter is written to the editable dataset assigned to the hemodialyzer, the hemofilter, or the ultrafilter, and is used to block use of the hemodialyzer, the hemofilter, or the ultrafilter in case the manufacturer of the hemodialyzer, the hemofilter, or the ultrafilter has detected a problem with the hemodialyzer, the hemofilter, or the ultrafilter, or storage conditions of the hemodialyzer, the hemofilter, or the ultrafilter or if environmental parameters have been outside the allowable limitations.

2. The process of claim 1, wherein more than one computer or computer network is accessed with the portable communication device.

3. The process of claim 1, wherein the remote computer or the computer network is selected from the group consisting of a computer or a computer network of the manufacturer of the hemodialyzer, the hemofilter, or the ultrafilter; a computer or a computer network of a hospital using the hemodialyzer, the hemofilter, or the ultrafilter; and a computer or a computer network used in performing supply chain management of the hemodialyzer, the hemofilter, or the ultrafilter.

4. The process of claim 1, wherein the portable communication device displays data from the editable dataset.

5. The process of claim 2, wherein the remote computer or the computer network is selected from the group consisting of a computer or a computer network of the manufacturer of the hemodialyzer, the hemofilter, or the ultrafilter; a computer or a computer network of a hospital using the hemodialyzer, the hemofilter, or the ultrafilter; and a computer or a computer network used in performing supply chain management of the hemodialyzer, the hemofilter, or the ultrafilter.

6. The process of claim 5, wherein the portable communication device displays data from the editable dataset.

7. The process of claim 2, wherein the portable communication device displays data from the editable dataset.

8. The process of claim 3, wherein the portable communication device displays data from the editable dataset.

9. The process of claim 1, further comprising the step of
   d) accessing at least one remote computer or computer network with the portable communication device, sending data previously read from the editable dataset to at least one remote computer or computer network, and writing data previously received from at least one remote computer or computer network to the editable dataset.

* * * * *